(12) United States Patent
Van Reusel et al.

(10) Patent No.: US 12,616,842 B2
(45) Date of Patent: May 5, 2026

(54) SELF-LOCKING FIXATION SYSTEM FOR MEDICAL IMPLANT

(71) Applicant: Cochlear Limited, Macquarie University (AU)

(72) Inventors: Floriaan Van Reusel, Mechelen (BE); Antonin Rambault, Mechelen (BE); Koen Erik Van Den Heuvel, Hove (BE)

(73) Assignee: Cochlear Limited, Macquarie University (AU)

( * ) Notice: Subject to any disclaimer, the term of this patent is extended or adjusted under 35 U.S.C. 154(b) by 242 days.

(21) Appl. No.: 18/695,089

(22) PCT Filed: Aug. 25, 2022

(86) PCT No.: PCT/IB2022/057981
§ 371 (c)(1),
(2) Date: Mar. 25, 2024

(87) PCT Pub. No.: WO2023/073445
PCT Pub. Date: May 4, 2023

(65) Prior Publication Data
US 2024/0408400 A1 Dec. 12, 2024

Related U.S. Application Data

(60) Provisional application No. 63/272,538, filed on Oct. 27, 2021.

(51) Int. Cl.
*A61N 1/375* (2006.01)
*A61N 1/36* (2006.01)

(52) U.S. Cl.
CPC ..... *A61N 1/37518* (2017.08); *A61N 1/36038* (2017.08)

(58) Field of Classification Search
CPC .............. A61N 1/0541; A61N 1/36036; A61N 1/36038; A61N 1/372; A61N 1/375
See application file for complete search history.

(56) References Cited

U.S. PATENT DOCUMENTS 6,325,755 B1 * 12/2001 Bushek ................ H04R 25/606
623/10
6,390,970 B1 5/2002 Muller
(Continued)

OTHER PUBLICATIONS

Supplementary Partial European Search Report for European Application No. EP22886223, dated Aug. 6, 2025.
(Continued)

*Primary Examiner* — Allen Porter
(74) *Attorney, Agent, or Firm* — Knobbe, Martens, Olson & Bear, LLP

(57) ABSTRACT

An apparatus includes an arm configured to be in mechanical communication with a transducer configured to be implanted within a recipient's body. The arm includes a first mating portion configured to engage and disengage with a plurality of second mating portions positioned along at least one longitudinal surface of a fixation element implanted within a portion of the recipient's body. The arm is configured to be moved between an unlocked state in which the arm is disengaged from the plurality of second mating portions and a locked state in which the arm is engaged with at least one of the second mating portions. The apparatus further includes at least one elastically deformable element configured to apply a restoring force to the arm such that the arm is in the locked state and to respond to an external force applied to the arm such that the arm is in the unlocked state.

28 Claims, 12 Drawing Sheets

(56)                References Cited

U.S. PATENT DOCUMENTS

| | | | |
|---|---|---|---|
| 7,326,171 B2 * | 2/2008 | Kasic, II | A61F 11/00 |
| | | | 600/25 |
| 2005/0228214 A1 | 10/2005 | Schneider | |
| 2007/0249890 A1 | 10/2007 | Muller et al. | |
| 2008/0300596 A1 | 12/2008 | Bernhard et al. | |
| 2010/0268313 A1 | 10/2010 | Conn | |
| 2013/0225912 A1 | 8/2013 | Leigh | |
| 2016/0059013 A1 | 3/2016 | Vlem | |

OTHER PUBLICATIONS

Search Report and Written Opinion received in International Application No. PCT/IB2022/057981, dated Dec. 1, 2022.

* cited by examiner

FIG. 5A:
FIG. 5B:
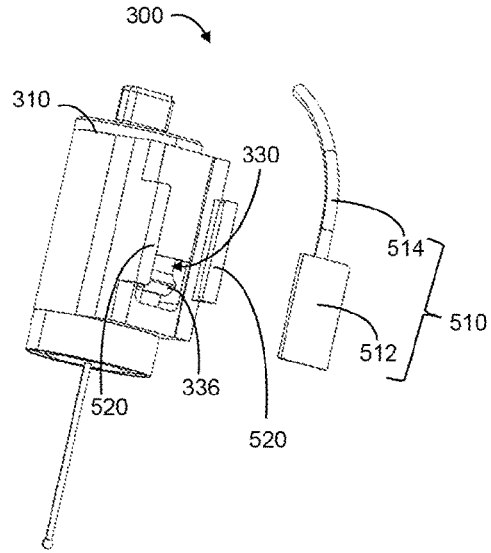
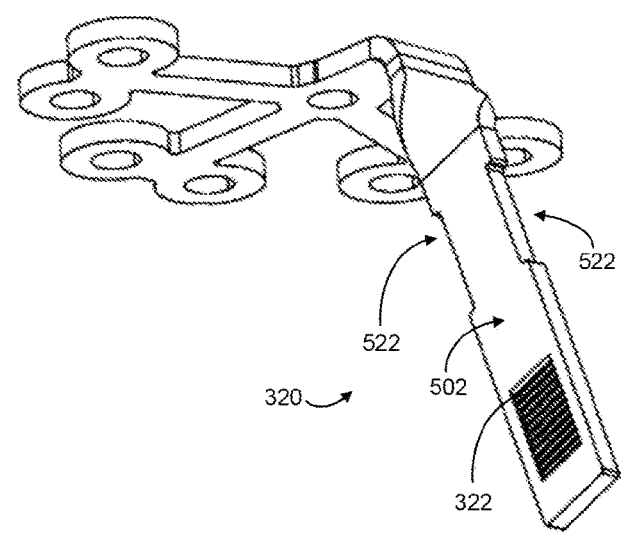

FIG. 6A:
FIG. 6B:
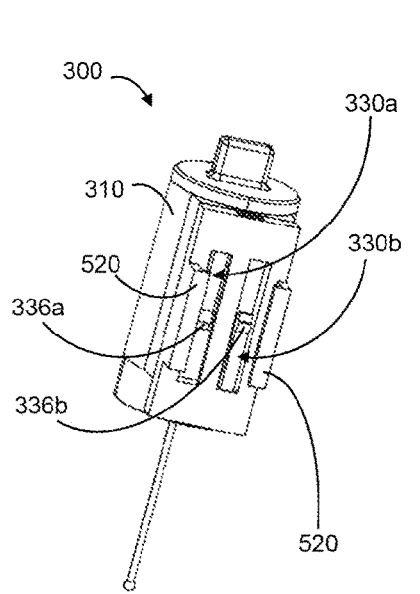
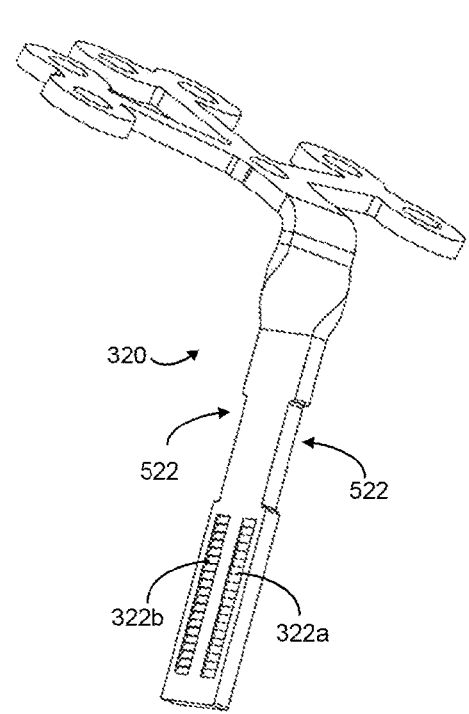

SELF-LOCKING FIXATION SYSTEM FOR MEDICAL IMPLANT

BACKGROUND

Field

The present application relates generally to medical implants (e.g., implantable medical prostheses) having active components (e.g., transducers; actuators; micro- phones; sensors).

Description of the Related Art

Medical devices have provided a wide range of therapeu- tic benefits to recipients over recent decades. Medical devices can include internal or implantable components/ devices, external or wearable components/devices, or com- binations thereof (e.g., a device having an external compo- nent communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement func- tions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symp- tom thereof, or to investigate, replace or modify the anatomy or a physiological process. Many of these functional devices utilize power and/or data received from external devices that are part of, or operate in conjunction with, implantable components.

SUMMARY

In one aspect disclosed herein, an apparatus comprises at least one arm comprising a first arm portion and a second arm portion. The first arm portion is configured to be in mechanical communication with a transducer configured to be implanted within a recipient's body. The second arm portion is spaced from the first arm portion and comprises at least one first mating portion configured to engage and disengage with a plurality of second mating portions posi- tioned along at least one longitudinal surface of a fixation element implanted within a portion of the recipient's body. The second arm portion is configured to be moved between an unlocked state in which the at least one first mating portion is disengaged from the plurality of second mating portions and a locked state in which the at least one first mating portion is engaged with at least one of the second mating portions. The apparatus further comprises at least one elastically deformable element configured to apply at least one restoring force to the at least one arm such that the second arm portion is in the locked state and to respond to at least one external force applied to the at least one arm such that the second arm portion is in the unlocked state.

In another aspect disclosed herein, an apparatus com- prises a transducer assembly configured to be implanted within the recipient's body and received by a bracket of a fixation element configured to be implanted within a portion of a recipient's body. The transducer assembly comprises a transducer configured to be implanted within a recipient's body. The transducer assembly further comprises at least one arm having a first portion mechanically coupled to an outer surface of the transducer assembly and a second portion spaced away from the first portion. The transducer assembly has a plurality of states comprising a first state and a second state. In the first state, the at least one arm is elastically bent to be substantially straight along the outer surface such that the transducer assembly is configured to be inserted and/or adjustably slid within the bracket along a sliding direction. In the second state, the second portion contacts an inner surface of the bracket and inhibits sliding of the transducer assembly within the bracket along the sliding direction.

In another aspect disclosed herein, a method comprises attaching a transducer assembly to a fixation element affixed to a location within a recipient's body. The method further comprises, while an unlocking force is applied to the trans- ducer assembly, slidably adjusting the position of the trans- ducer assembly relative to the fixation element such that the transducer assembly is at a location at which the transducer assembly is configured to be operationally coupled to a target portion of the recipient's body. The method further comprises, upon the transducer assembly being at the loca- tion, ceasing applying the unlocking force to the transducer assembly such that the transducer assembly self-locks to the fixation element at the location.

In another aspect disclosed herein, an apparatus com- prises a fixation element configured to be affixed to a fixation location on and/or within a recipient's body. The fixation element comprises at least one surface and a plurality of protrusions and/or recesses positioned along the at least one surface. The plurality of protrusions and/or recesses is configured to engage and disengage with at least one recess and/or protrusion of at least one arm of a transducer assem- bly configured to be implanted within the recipient's body. The transducer assembly comprises a transducer configured to be in operational communication with a target portion of the recipient's body. The target portion is spaced from the fixation location. The plurality of protrusions and/or recesses provide a plurality of discrete locations at which the transducer assembly can be selectively automatically locked to the fixation element.

BRIEF DESCRIPTION OF THE DRAWINGS

Implementations are described herein in conjunction with the accompanying drawings, in which:

FIGS. 5A-5E schematically illustrate another example apparatus in accordance with certain implementations described herein;

FIGS. 6A-6B schematically illustrate another example apparatus in accordance with certain implementations described herein;

DETAILED DESCRIPTION

Figure 1:
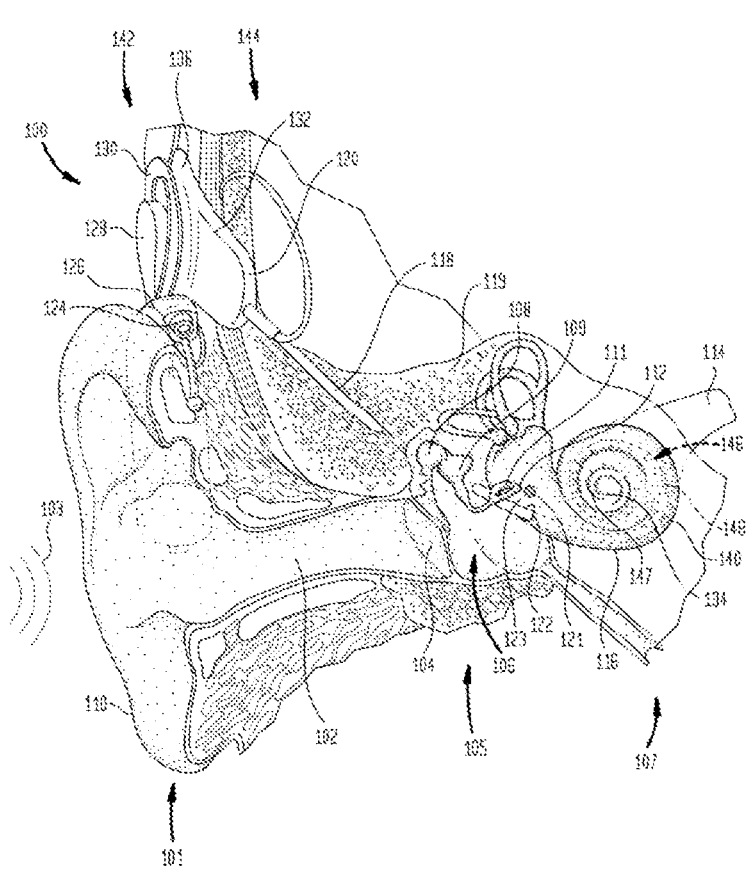
FIG. 1 is a perspective view of an example cochlear implant auditory prosthesis implanted in a recipient in accordance with certain implementations described herein.

Certain implementations described herein provide a fixation system for a transducer assembly comprising an active component (e.g., microphone; tube microphone; actuator; middle ear actuator) that is readily adjusted along a bone fixture to be in an operational position relative to a target portion of the recipient's body and to easily lock to the bone fixture once the transducer assembly has been suitably positioned. The fixation system includes at least one resiliently bendable or rotatable arm that is biased away from the bone fixture by an external force and/or a removable element to allow the transducer assembly to be adjusted along the bone fixture and that engages with the bone fixture upon removal of the external force and/or the removable element, thereby self-locking or automatically locking the transducer assembly to the selected location on the bone fixture. Certain such fixation systems can simplify the implantation process, leading to time- and/or cost-savings.

The teachings detailed herein are applicable, in at least some implementations, to any type of implantable medical system utilizing an implantable transducer assembly configured to provide stimulation signals and/or medicament dosages to a portion of the recipient's body in response to received information and/or control signals (e.g., implantable sensor prostheses; implantable stimulation system; implantable medicament administration system). For example, the implantable medical system can comprise an auditory prosthesis system configured to generate and apply stimulation signals that are perceived by the recipient as sounds (e.g., evoking a hearing percept). Such implantable transducer assemblies can include but are not limited to: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other types of auditory prosthesis devices (e.g., auditory brain stimulators), and/or combinations or variations thereof, or any other suitable hearing prosthesis system with or without one or more external components. Merely for ease of description, apparatus and methods disclosed herein are primarily described with reference to an illustrative auditory prosthesis system, namely a middle ear implant, but implementations can include any type of auditory prosthesis that can utilize the teachings detailed herein and/or variations thereof. Certain such implementations can be referred to as "partially implantable," "semi-implantable," "mostly implantable," "fully implantable," or "totally implantable" auditory prostheses.

The teachings detailed herein and/or variations thereof may also be used with a variety of other medical devices that provide a wide range of therapeutic benefits to recipients, patients, or other users. For example, other sensory prosthesis systems that are configured to evoke other types of neural or sensory (e.g., sight, tactile, smell, taste) percepts are compatible with certain implementations described herein, including but are not limited to: vestibular devices (e.g., vestibular implants), visual devices (e.g., bionic eyes), visual prostheses (e.g., retinal implants), somatosensory implants, and chemosensory implants. In some implementations, the teachings detailed herein and/or variations thereof can be utilized in other types of implantable medical devices beyond sensory prostheses. For example, apparatus and methods disclosed herein and/or variations thereof can be used with one or more of the following: sensors; cardiac pacemakers; drug delivery systems; defibrillators; functional electrical stimulation devices; catheters; brain implants; seizure devices (e.g., devices for monitoring and/or treating epileptic events); sleep apnea devices; electroporation; pain relief devices; etc. Implementations can include any type of medical system that can utilize the teachings detailed herein and/or variations thereof (e.g., systems that may benefit from having an adjustable orientation of at least a portion of the implanted device during implantation).

FIG. 1 is a perspective view of an example cochlear implant auditory prosthesis 100 implanted in a recipient in accordance with certain implementations described herein. The example auditory prosthesis 100 is shown in FIG. 1 as comprising an implanted stimulator unit 120 and a microphone assembly 124 that is external to the recipient (e.g., a partially implantable cochlear implant). An example auditory prosthesis 100 (e.g., a totally implantable cochlear implant: a mostly implantable cochlear implant) in accordance with certain implementations described herein can replace the external microphone assembly 124 shown in FIG. 1 with a subcutaneously implantable microphone assembly, as described more fully herein. In certain implementations, the example cochlear implant auditory prosthesis 100 of FIG. 1 can be in conjunction with a reservoir of liquid medicament as described herein.

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone 124) for detecting sound, a sound processing unit 126 (e.g., disposed in a Behind-The-Ear unit), a power source (not shown), and an external transmitter unit 128. In the illustrative implementations of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144. The sound processing unit 126 processes the output of the microphone 124 that is positioned externally to the recipient's body, in the depicted implementation, by the recipient's auricle 110. The sound processing unit 126 processes the output of the microphone 124 and generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some implementations, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and, preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some implementations, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other implementations, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-ear-canal microphone) implantable on or within the recipient, and can be referred to as a mostly implantable cochlear implant ("MICI").

Figure 2:
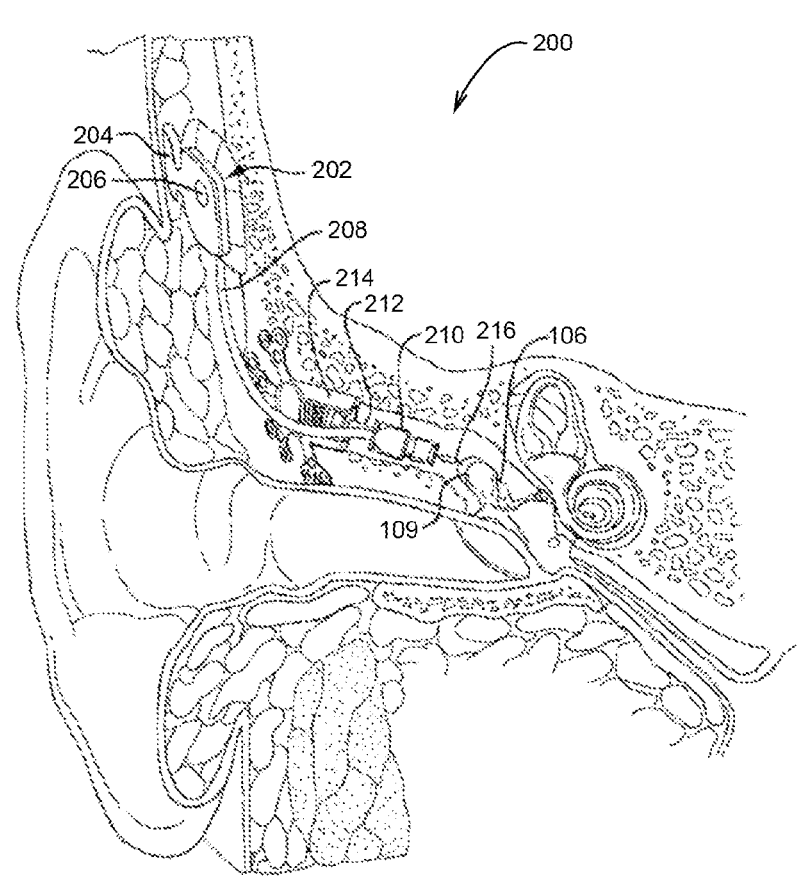
FIG. 2 is a perspective view of an example fully implant- able middle ear implant auditory prosthesis implanted in a recipient in accordance with certain implementations described herein.

FIG. 2 schematically illustrates a perspective view of an example fully implantable auditory prosthesis 200 (e.g., fully implantable middle ear implant or totally implantable acoustic system), implanted in a recipient, utilizing an acoustic actuator in accordance with certain implementations described herein. The example auditory prosthesis 200 of FIG. 2 comprises a biocompatible implantable assembly 202 (e.g., comprising an implantable capsule) located subcutaneously (e.g., beneath the recipient's skin and on a recipient's skull). While FIG. 2 schematically illustrates an example implantable assembly 202 comprising a microphone, in other example auditory prostheses 200, a pendant microphone can be used (e.g., connected to the implantable assembly 202 by a cable). The implantable assembly 202 includes a signal receiver 204 (e.g., comprising a coil element) and an acoustic transducer 206 (e.g., a microphone comprising a diaphragm and an electret or piezoelectric transducer) that is positioned to receive acoustic signals through the recipient's overlying tissue. The implantable assembly 202 may further be utilized to house a number of components of the fully implantable auditory prosthesis 200. For example, the implantable assembly 202 can include an energy storage device and a signal processor (e.g., a sound processing unit). Various additional processing logic and/or circuitry components can also be included in the implantable assembly 202 as a matter of design choice.

For the example auditory prosthesis 200 shown in FIG. 2, the signal processor of the implantable assembly 202 is in operative communication (e.g., electrically interconnected via a wire 208) with an actuator 210 (e.g., comprising a transducer configured to generate mechanical vibrations in response to electrical signals from the signal processor). In certain implementations, the example auditory prosthesis 100, 200 shown in FIGS. 1 and 2 can comprise an implantable microphone assembly, such as the microphone assembly 206 shown in FIG. 2. For such an example auditory prosthesis 100, the signal processor of the implantable assembly 202 can be in operative communication (e.g., electrically interconnected via a wire) with the microphone assembly 206 and the stimulator unit of the main implantable component 120. In certain implementations, at least one of the microphone assembly 206 and the signal processor (e.g., a sound processing unit) is implanted on or within the recipient.

The actuator 210 of the example auditory prosthesis 200 shown in FIG. 2 is supportably connected to a positioning system 212, which in turn, is connected to a bone anchor 214 mounted within the recipient's mastoid process (e.g., via a hole drilled through the skull). The actuator 210 includes a connection apparatus 216 for connecting the actuator 210 to the ossicles 106 of the recipient. In a connected state, the connection apparatus 216 provides a communication path for acoustic stimulation of the ossicles 106 (e.g., through transmission of vibrations from the actuator 210 to the incus 109).

During normal operation, ambient acoustic signals (e.g., ambient sound) impinge on the recipient's tissue and are received transcutaneously at the microphone assembly 206. Upon receipt of the transcutaneous signals, a signal processor within the implantable assembly 202 processes the signals to provide a processed audio drive signal via wire 208 to the actuator 210. As will be appreciated, the signal processor may utilize digital processing techniques to provide frequency shaping, amplification, compression, and other signal conditioning, including conditioning based on recipient-specific fitting parameters. The audio drive signal causes the actuator 210 to transmit vibrations at acoustic frequencies to the connection apparatus 216 to affect the desired sound sensation via mechanical stimulation of the incus 109 of the recipient.

The subcutaneously implantable microphone assembly 202 is configured to respond to auditory signals (e.g., sound; pressure variations in an audible frequency range) by generating output signals (e.g., electrical signals; optical signals; electromagnetic signals) indicative of the auditory signals received by the microphone assembly 202, and these output signals are used by the auditory prosthesis 100, 200 to generate stimulation signals which are provided to the recipient's auditory system. To compensate for the decreased acoustic signal strength reaching the microphone assembly 202 by virtue of being implanted, the diaphragm of an implantable microphone assembly 202 can be configured to provide higher sensitivity than are external non-implantable microphone assemblies. For example, the diaphragm of an implantable microphone assembly 202 can be configured to be more robust and/or larger than diaphragms for external non-implantable microphone assemblies.

The example auditory prostheses 100 shown in FIG. 1 utilizes an external microphone 124 and the auditory prosthesis 200 shown in FIG. 2 utilizes an implantable microphone assembly 206 comprising a subcutaneously implantable acoustic transducer. In certain implementations described herein, the auditory prosthesis 100 utilizes one or more implanted microphone assemblies on or within the recipient. In certain implementations described herein, the auditory prosthesis 200 utilizes one or more microphone assemblies that are positioned external to the recipient and/or that are implanted on or within the recipient, and utilizes one or more acoustic transducers (e.g., actuator 210) that are implanted on or within the recipient. In certain implementations, an external microphone assembly can be used to supplement an implantable microphone assembly of the auditory prosthesis 100, 200. Thus, the teachings detailed herein and/or variations thereof can be utilized with any type of external or implantable microphone arrangement, and the acoustic transducers shown in FIGS. 1 and 2 are merely illustrative.

FIGS. 3A-3E schematically illustrate various views of an example apparatus 300 in accordance with certain implementations described herein. The apparatus 300 can be configured to affix a transducer 310 configured to be implanted within a recipient's body onto a fixation element 320 implanted within a portion of the recipient's body. The apparatus 300 comprises at least one arm 330 comprising a first arm portion 332 configured to be in mechanical communication with the transducer 310 and a second arm portion 334 spaced from the first arm portion 332. The second arm portion 334 comprises at least one first mating portion 336 configured to engage and disengage with a plurality of second mating portions 322 positioned along at least one longitudinal surface 324 of the fixation element 320. The second arm portion 334 is configured to be moved between an unlocked state in which the at least one first mating portion 336 is disengaged from the plurality of second mating portions 322 and a locked state in which the at least one first mating portion 336 is engaged with at least one of the second mating portions 322. The apparatus 300 further comprises at least one elastically deformable element 340 configured to apply at least one restoring force 342 to the at least one arm 330 such that the second arm portion 334 is in the locked state and to respond to at least one external force 350 applied to the at least one arm 330 such that the second arm portion 334 is in the unlocked state.

FIGS. 3A-3E schematically illustrate an example implementation in which the at least one arm 330 comprises first and second arms 330 configured to be positioned on opposite longitudinal surfaces 324 of the fixation element 320 and the fixation element 320 comprises a pair of longitudinal surfaces 324 with corresponding pluralities of second mating portions 322 on opposite sides of the fixation element 320. In certain other implementations, the fixation element 320 comprises a single longitudinal surface 324 with a single plurality of second mating portions 322 or comprises two or more longitudinal surfaces 324 on opposite or adjacent sides of the fixation element 320, each longitudinal surface 324 having a corresponding plurality of second mating portions 322.

Figures 3A, 3B, 3C:
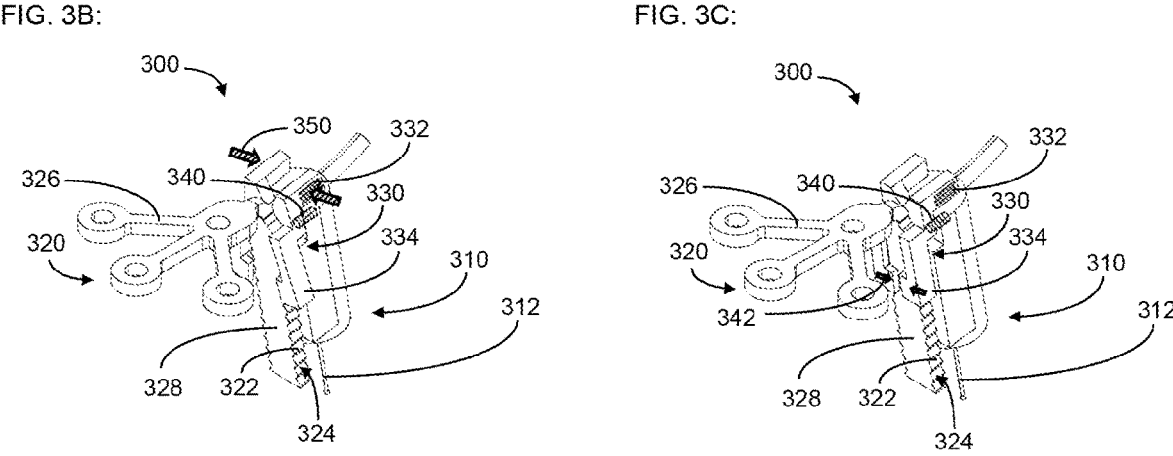
FIGS. 3A-3E schematically illustrate various views of an example apparatus in accordance with certain implementa- tions described herein.
Figure 3D:
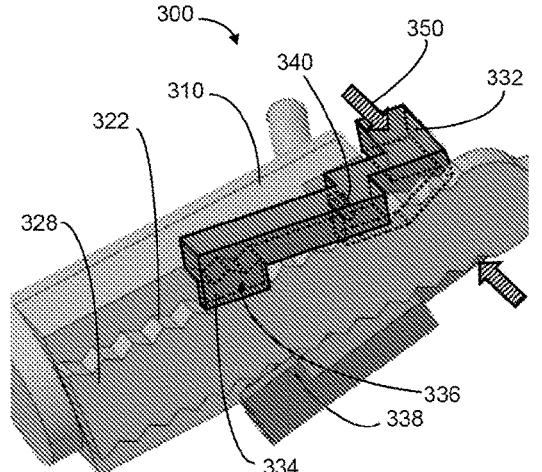
Figure 3E:
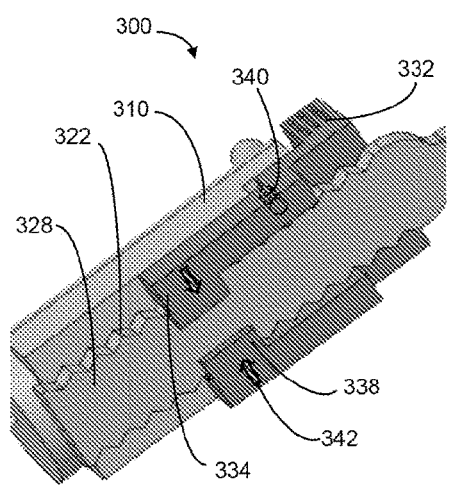

FIG. 3A shows the example apparatus 300 separated from the fixation element 320. For example, the apparatus 300 can be held by a tool (e.g., tweezers; not shown) being manipulated by a practitioner during the implantation process, by which the tool applies the at least one external force 350 (e.g., squeezing the two first arm portions 332 towards one another) which counteracts the at least one restoring force 342 such that the two second arm portions 344 are in the unlocked state. FIGS. 3B and 3D show two views of the example apparatus 300 placed onto the fixation element 320 while the at least one external force 350 is being applied to the apparatus 300. In the configuration shown in FIGS. 3B and 3D, the apparatus 300 can be moved along the fixation element 320 (e.g., along the longitudinal surfaces 324) so as to position the apparatus 300 at an operative location (e.g., a location at which the apparatus 300 is to be in operative communication with the target portion of the recipient's body). FIGS. 3C and 3E show two views of the example apparatus 300 placed onto the fixation element 320 without the at least one external force 350 being applied to the apparatus 300, such that the at least one restoring force 342 places the two second arm portions 344 in a locked state, with the apparatus 300 affixed to the fixation element 320 at the operative location.

In certain implementations, the transducer 310 comprises an active component (e.g., actuator; microphone; optical sensor; magnetic induction sensor) configured to be in operative communication with a target portion of the recipient's body (e.g., an ossicle 106, a portion of a cochlea 140, a portion of the otic capsule, or a semicircular canal of the recipient's body). For example, the transducer 310 can comprise an acoustic actuator (e.g., actuator 210) configured to generate mechanical vibrations at acoustic frequencies in response to electrical signals from a signal processor and to transmit the vibrations (e.g., via a connection apparatus 216) to the ossicles 106 of the recipient. For another example, the transducer 310 can comprise a microphone configured to sense or detect mechanical vibrations from a portion of the recipient's body (e.g., the ossicles 106) and to generate electrical and/or optical signals in response.

In certain implementations, the active component of the transducer 310 is in mechanical communication with the target portion of the recipient's body via a rod, tube, wire or other elongate member 312 comprising a biocompatible material (e.g., titanium; titanium alloy; plastic; ceramic) and extending from an end portion of the transducer 310 (e.g., having a length in a range of 5 millimeters to 40 millimeters; in a range of 5 millimeters to 15 millimeters). The elongate member 312 can be configured to be in mechanical communication with the target portion of the recipient's body such that mechanical vibrations propagate along the elongate member 312 between the transducer 310 and the target portion of the recipient's body). In certain other implementations, the active component of the transducer 310 comprises a sensor (e.g., optical sensor; magnetic induction sensor) facing towards the target portion of the recipient's body and configured to sense or detect motion (e.g., vibrations) of the target portion of the recipient's body. While certain implementations are described herein as comprising a transducer 320, in certain other implementations, the apparatus 300 comprises a different component (e.g., reservoir; valve; pump) configured to be in operative communication with the target portion of the recipient's body via an elongate conduit 312 comprising a fluid conduit (e.g., tube) configured to provide at least one liquid medicament to the target portion of the recipient's body.

In certain implementations, the fixation element 320 (e.g., bone anchor 214) comprises a first portion 326 comprising a biocompatible material (e.g., titanium; titanium alloy; plastic; ceramic) configured to be affixed (e.g., via screws, sutures, adhesive and/or osseointegration) to a first location on and/or within the recipient's body (e.g., beneath the recipient's skin and on a recipient's skull; a machined surface of the skull bone). The fixation element 320 can further comprise a second portion 328 comprising a biocompatible material (e.g., titanium; titanium alloy; plastic; ceramic) extending from the first portion 322 towards a target portion of the recipient's body (e.g., through a hole drilled through the skull; in an inner ear region; in a middle ear region; within a cochleovestibular region; to an ossicle 106; to a cochlea 140), the second portion 328 configured to hold the transducer 320. In certain implementations, the first portion 326 and the second portion 328 are integral with one another, while in certain other implementations, the first portion 326 and the second portion 328 are separate components that are affixed to one another. The transducer 310 can comprise a middle ear transducer assembly with the first portion 326 of the fixation element 320 (e.g., bracket) affixed to a surface of the recipient's skull bone (e.g., outer surface; top surface) and the second portion 328 of the fixation element 320 can extend at least partially within a region (e.g., middle ear region; mastoid bone cavity; channel; cavity; naturally-occurring; drilled or otherwise formed through surgical techniques) extending through the skull bone of the recipient. The transducer 310 can be in mechanical communication with the fixation element 320 and in operative communication with the target portion of the recipient's body (e.g., an ossicle 106; incus 109) spaced from the fixation element 320.

In certain implementations, the second portion 328 of the fixation element 320 is configured to be adjusted to modify a position (e.g., linear position; depth) and/or orientation of the longitudinal surface 324 (e.g., relative to the target portion of the recipient's body; during implantation of the apparatus 300). For example, the second portion 328 of certain implementations is configured to be plastically deformed (e.g., bent and/or twisted; controlled by a practitioner during implantation of the apparatus 300) such that the second mating portions 322 of the longitudinal surface 324 are aligned along a direction towards the target portion of the recipient's body.

In certain implementations, the plurality of second mating portions 322 comprises a plurality of protrusions and/or recesses that extend along the longitudinal surface 324 (e.g., along a distance in a range of 10 millimeters to 20 millimeters; having a period between adjacent second mating portions 322 in a range of 0.2 millimeter to 2 millimeters). In certain implementations, the first mating portion 336 of the second arm portion 334 comprises at least one protrusion and/or recess configured to mate (e.g., engage) with at least one of the second mating portions 322. For example, as schematically illustrated by FIGS. 3A-3E, the plurality of second mating portions 322 can comprise a plurality of teeth along the longitudinal surface 324, and the first mating portion 336 can comprise at least one tooth configured to engage with the at least one second mating portion 322 when the second arm portion 334 is in the locked state and configured to not engage with (e.g., disengage from) the plurality of second mating portions 322 when the second arm portion 334 is in the unlocked state.

In certain implementations, the at least one arm 330 is integral with a housing of the transducer 310 or is integral with an attachment element configured to be affixed to the housing of the transducer 310, while in certain other implementations, the at least one arm 330 is a separate component that is configured to be affixed to the housing of the transducer 310 or to an attachment element configured to be affixed to the housing of the transducer 310. In certain implementations, the at least one arm 330 comprises a single arm 330, while in certain other implementations, the at least one arm 330 comprises two or more arms 330. The at least one arm 330 of certain implementations comprises a biocompatible material (e.g., titanium; titanium alloy; plastic; ceramic). In certain implementations, the first arm portion 332 and the second arm portion 334 are integral with one another, while in certain other implementations, the first arm portion 332 and the second arm portion 334 are separate components that are affixed to one another.

In certain implementations, the first arm portion 332 is configured to be moved (e.g., rotated; deflected) relative to the transducer 310 such that the second arm portion 334 moves (e.g., rotates; deflects) relative to the longitudinal surface 324 of the fixation element 320. For example, as schematically illustrated by FIGS. 3A-3E, the at least one arm 330 can comprise a pivot (not shown) between the first arm portion 332 (e.g., tab) and the second arm portion 334, the first arm portion 332 configured to receive the at least one external force 350 and to move the second arm portion 334. The two first arm portions 332 of FIGS. 3A-3E respond to the at least one external force 350 selectively applied to the two first arm portions 332 by moving towards one another and by moving the two second arm portions 334 of the first and second arms 330 to the unlocked state.

In certain implementations, the at least one elastically deformable element 340 (e.g., at least one compression spring; at least one extension spring; at least one torsion spring) configured to apply the at least one restoring force 342 to the at least one arm 330. For example, for an arm 330 comprising a pivot, the at least one elastically deformable element 342 can comprise a torsion spring concentric with the pivot and mechanically coupled to the at least one arm 330 (FIGS. 3A-3E only show the torsion spring of one of the two arms 330). For another example, the at least one elastically deformable element 340 can comprise a resilient portion of the arm 330 (e.g., configured to be resiliently bent and/or rotated relative to the transducer 310 upon the at least one external force 350 being applied to the arm 330).

In certain implementations, the at least one elastically deformable element 340 comprises a separate spring for each arm 330, while in certain other implementations, the at least one elastically deformable element 340 comprises a spring that applies the at least one restoring force 342 to two or more arms 330 concurrently. In certain implementations, the at least one elastically deformable element 340 applies the at least one restoring force 342 both while the second arm portion 334 is in the unlocked state (e.g., the restoring force 342 returning the second arm portion 334 to the locked state) and while the second arm portion 334 is in the locked state (e.g., the restoring force 342 pressing the at least one first mating portion 336 against the second mating portions 322), while in certain other implementations, the at least one elastically deformable element 340 applies the at least one restoring force 342 only while the second arm portion 334 is not in the locked state (e.g., the restoring force 342 returning the second arm portion 334 to the locked state and resisting movement of the second arm portion 334 from the locked state).

In certain implementations, the at least one arm 330 and the at least one elastically deformable element 340 are configured such that the tool (not shown) that applies the at least one external force 350 presses the two first arm portions 332 towards one another (e.g., as schematically illustrated by FIGS. 3A-3E), while in certain other implementations, the at least one arm 330 and the at least one elastically deformable element 340 are configured such that the tool presses the two first arm portions 332 away from one another.

In certain implementations, the transducer 310 is configured to be moved (e.g., controllably slid) along the fixation element 320 while the second arm portion 334 is in the unlocked state and to be fixed at (e.g., unmovable from) a position along the fixation element 320 while the second arm portion 334 is in the locked state. The plurality of second mating portions 322 along the fixation element 320 provide a plurality of discrete locations of the apparatus 300 at which the second arm portion 334 can be placed in the locked state (e.g., holding the apparatus 300 in place). In certain implementations, as schematically illustrated by FIGS. 3A-3E, each of the first and second arms 330 comprises an extension 338 configured to extend at least partially across a first surface of the fixation element 320 opposite to a second surface facing the transducer 310. For example, the first and second arms 330 can be placed in an intermediate position (e.g., between positions corresponding to being fully coupled or affixed to the fixation element 320 and being fully decoupled to the fixation element 320), the intermediate position configured to have the extensions 338 extending at least partially across the first surface without the first mating portions 336 engaging with the second mating portions 322, thereby holding the apparatus 300 in slidable mechanical communication with the fixation element 320.

Figure 4A:
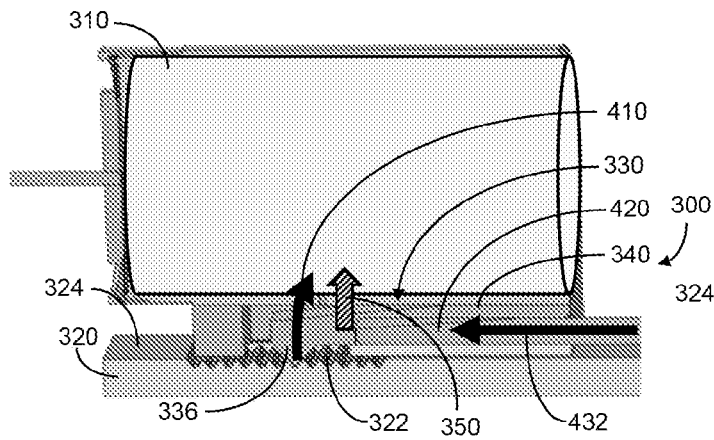
FIGS. 4A-4B schematically illustrate another example apparatus in accordance with certain implementations described herein.
Figure 4B:
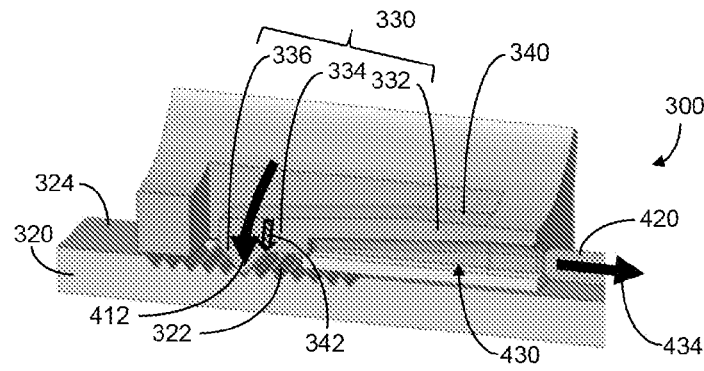

FIGS. 4A-4B schematically illustrate another example apparatus 300 in accordance with certain implementations described herein. The apparatus 300 of FIGS. 4A-4B can be configured to affix a transducer 310 configured to be implanted within a recipient's body onto a fixation element 320 implanted within a portion of the recipient's body. The apparatus 300 of FIGS. 4A-4B comprises an arm 330 comprising a first arm portion 332 configured to be in mechanical communication with the transducer 310 and a second arm portion 334 spaced from the first arm portion 332. The second arm portion 334 comprises at least one first mating portion 336 (e.g., at least one protrusion and/or recess; at least one tooth; at least one snaphook) configured to engage and disengage with a plurality of second mating portions 322 (e.g., a plurality of protrusions and/or recesses; a plurality of teeth) positioned along at least one longitudinal surface 324 of the fixation element 320. The second arm portion 334 is configured to be moved between an unlocked state in which the at least one first mating portion 336 is disengaged from the plurality of second mating portions 322 and a locked state in which the at least one first mating portion 336 is engaged with at least one of the second mating portions 322. In certain implementations, the arm 330 and the at least one first mating portion 336 operate as a pawl of a rachet with the plurality of second mating portions 322.

The apparatus 300 of FIGS. 4A-4B further comprises an elastically deformable element 340 that comprises a resilient portion of the arm 330 (e.g., at least a portion of the first arm portion 332) that is configured to respond to at least one external force 350 applied to the arm 330 such that the second arm portion 334 is disengaged from (e.g., not mated with) the plurality of second mating portions 322 (e.g., when the second arm portion 334 is in an unlocked state). The resilient portion of the arm 330 is further configured to apply at least one restoring force 342 to the arm 330 such that the at least one first mating portion 336 is engaged (e.g., mated) with the plurality of second mating portions 322 (e.g., when the second arm portion 334 is in a locked state). Without the external forces 350 applied to the arm 330, the resilient portion of the arm 330 has the at least one first mating portion 336 engaged (e.g., mated) with the plurality of second mating portions 322 (e.g., the locked state of the second arm portion 334 is a default state such that the apparatus 300 is self-locking or automatically locks to the fixation element 320).

In certain implementations, the resilient portion of the arm 330 is configured to be resiliently bent so as to move the second arm portion 334 away from the plurality of second mating portions 322 (e.g., in a direction 410). For example, as schematically illustrated by FIG. 4A, the resilient portion can be resiliently bent by an elongate tool 420 (e.g., pin;

wire) within a hollow region 430 bounded at least partially by the arm 330 (e.g., the hollow region 430 between the arm 330 and the fixation element 320; the hollow region 430 within an attachment element configured to be affixed to the housing of the transducer 310). In certain implementations, the elongate tool 420 is initially within the hollow region 430 when a practitioner (e.g., surgeon) receives the apparatus 300, while in certain other implementations, the elongate tool 420 can be inserted into the hollow region 430 (e.g., along a direction 432) by the practitioner (e.g., during implantation of the apparatus 300 and the transducer 310). With the elongate tool 420 within the hollow region 430 (thereby applying the external force 350 to the arm 330 so as to resiliently bend the resilient portion), the apparatus 300 is disengaged from the fixation element 320. While disengaged, the position of the apparatus 300 and the transducer 310 can be controllably adjusted along the fixation element 320 (e.g., closer to or farther from the target portion), thereby allowing the practitioner to adjust (e.g., select) the operational position of the apparatus 300 and the transducer 310.

In certain implementations, the elongate tool 420 can be withdrawn from the hollow region 430 (e.g., along a direction 434) by the practitioner (see, e.g., FIG. 4B). With the elongate tool 420 withdrawn (e.g., the external force 350 no longer applied to the arm 330), the resilient portion of the arm 330 moves (e.g., in a direction 412) such that the at least one first mating element 336 engages (e.g., mates) with the plurality of second mating elements 322, thereby affixing (e.g., locking) the apparatus 300 and the transducer 310 at the selected operational position.

Figures 5C, 5D, 5E:
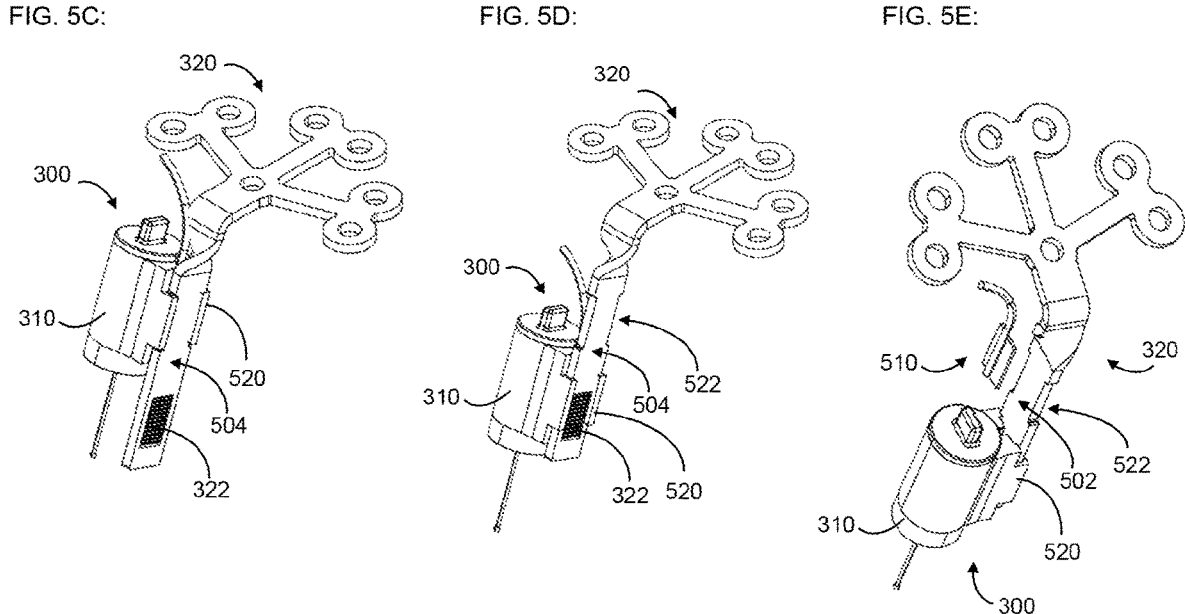

FIGS. 5A-5E schematically illustrate another example apparatus 300 in accordance with certain implementations described herein. FIG. 5A schematically illustrates a partially exploded view of the apparatus 300 and FIG. 5B schematically illustrates an example fixation element 320 configured to have the apparatus 300 affixed thereto in accordance with certain implementations described herein. FIGS. 5C-5E schematically illustrate various configurations of the apparatus 300 and the fixation element 320 during an example implantation process in accordance with certain implementations described herein. In certain implementations, the at least one arm 330 and the at least one first mating portion 336 operate as a pawl of a rachet with the plurality of second mating portions 322.

In certain implementations, the plurality of second mating elements 322 are on a single surface of the fixation element 320, while in certain other implementations (e.g., as schematically illustrated by FIGS. 5B-5E), a first set of the second mating elements 322 are on a first surface 502 of the fixation element 320 and a second set of the second mating elements 322 are on a second surface 504 of the fixation element 320 (e.g., the second surface 504 opposite to the first surface 502). By having second mating elements 322 on multiple surfaces of the fixation element 320, certain implementations provide additional options for attaching the apparatus 300 to the fixation element 320.

In certain implementations, the apparatus 300 comprises a removable element 510 comprising a first portion 512 (e.g., plate) and a second portion 514 (e.g., wire; rod) affixed to the first portion 512. The first portion 512 is configured to be between the at least one first mating portion 336 (e.g., at least one protrusion and/or recess; at least one tooth; at least one snaphook) of the at least one arm 330 and the plurality of second mating portions 322 (e.g., a plurality of protrusions and/or recesses; a plurality of teeth) of the fixation element 320, thereby preventing the at least one first mating portion 336 from engaging (e.g., mating) with at least one of the second mating portions 322. The first portion 512 is further configured to be removed from between the at least one first mating portion 336 and the plurality of second mating portions 322, thereby allowing the at least one first mating portion 336 to engage (e.g., mate) with at least one of the second mating portions 322. FIG. 5A schematically illustrates a partially exploded view of the apparatus 300 by showing the removable element 510 spaced away from the other components of the apparatus 300.

In certain implementations, the apparatus 300 further comprises at least one retention element 520 (e.g., tab; key) configured to fit onto the fixation element 320 while allowing the apparatus 300 to be slidably adjusted among various positions along the fixation element 320. For example, as schematically illustrated by FIG. 5B, the fixation element 320 can comprise at least one recess 522 at a first location along the fixation element 320, the at least one recess 522 configured to receive the at least one retention element 520 such that the apparatus 300 can be slidably adjusted along the fixation element 320 away from the at least one recess 522 and towards the plurality of second mating portions 322.

During an example implantation process, schematically illustrated by FIGS. 5C-5E, the apparatus 300 can initially be separate from the fixation element 320 (e.g., while the fixation element 320 is being affixed to a portion of the recipient's body). Once the fixation element 320 is at least partially affixed to the recipient's body (e.g., by the practitioner), the apparatus 300 can be placed on the fixation element 320 by moving the apparatus 300 (e.g., by the practitioner) such that the at least one retention element 520 is received by the at least one recess 522 (see, e.g., FIG. 5C). The apparatus 300 can then be slidably moved along the fixation element 320 (e.g., by the practitioner) away from the at least one recess 522 such that the at least one retention element 520 keeps the apparatus 300 in slidable contact with the fixation element 320 (e.g., inhibiting the apparatus 300 from separating from the fixation element 320) (see, e.g., FIG. 5D). Once the apparatus 300 is at an operational position along the fixation element 320, the removable element 510 can be removed from the apparatus 300 (e.g., by the practitioner), thereby allowing the at least one first mating element 336 to engage (e.g., mate) with at least one of the second mating elements 322 so as to lock (e.g., self-lock; automatically lock) onto the fixation element 320 at the operational position (see, e.g., FIG. 5E).

FIGS. 6A-6B schematically illustrate another example apparatus 300 in accordance with certain implementations described herein. FIG. 6A schematically illustrates the apparatus 300 comprising two arms 330*a,b*, each comprising a corresponding first mating element 336*a,b*. FIG. 6B schematically illustrates an example fixation element 320 configured to have the apparatus 300 affixed thereto and comprising two pluralities of second mating elements 322*a,b* in accordance with certain implementations described herein. In certain implementations, the arm 330*a* and the at least one first mating portion 336*a* operate as a pawl of a rachet with the plurality of second mating portions 322*a* (e.g., inhibiting sliding of the apparatus 300 along the fixation element 320 in a first direction), and the arm 330*b* and the at least one first mating portion 336*b* operate as a pawl of a rachet with the plurality of second mating portions 322*b* (e.g., inhibiting sliding of the apparatus 300 along the fixation element 320 in a second direction opposite to the first direction).

Figures 7A, 7B:
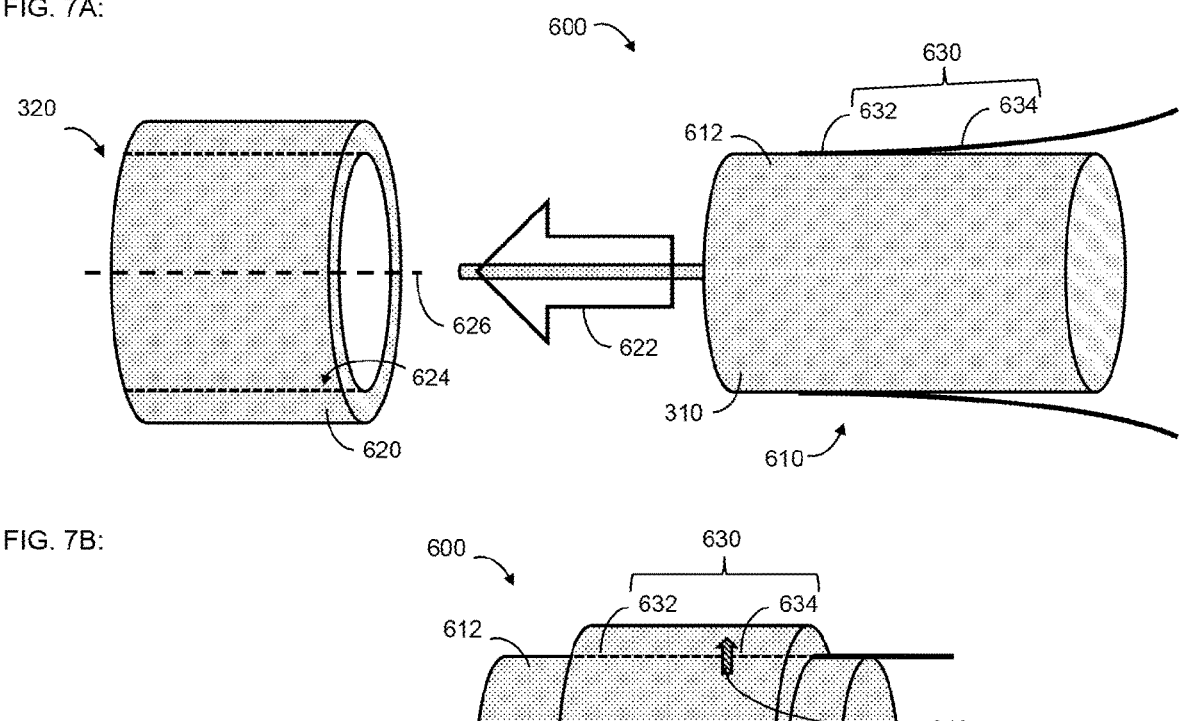
FIGS. 7A and 7B schematically illustrate an example apparatus in accordance with certain implementations described herein.

FIGS. 7A and 7B schematically illustrate an example apparatus 600 in accordance with certain implementations described herein. FIGS. 7A and 7B shows the example apparatus 600 prior to and after being affixed, respectively, to the fixation element 320. The apparatus 600 comprises a transducer assembly 610 configured to be implanted within the recipient's body and received by a bracket 620 (e.g., collar) of a fixation element 320 configured to be implanted within a portion of a recipient's body. The transducer assembly 610 comprises a transducer 310 configured to be implanted within a recipient's body. The transducer assembly 610 further comprises at least one arm 630 (e.g., an elastically bendable leaf spring; springlike tab) having a first portion 632 (e.g., end portion) mechanically coupled to an outer surface 612 of the transducer assembly 610 (e.g., an outer surface of a housing of the transducer 310) and a second portion 634 spaced away from the first portion 632. The transducer assembly 610 has a plurality of states (e.g., configurations) comprising a first state and a second state. In the first state, the at least one arm 630 is elastically bent to be substantially straight along the outer surface 612 such that the transducer assembly 610 is configured to be inserted and/or adjustably slid within the bracket 620 (e.g., along a sliding direction 622). In the second state, the second portion 634 contacts an inner surface 624 of the bracket 620 and inhibits sliding of the transducer assembly 610 within the bracket 620 (e.g., along the sliding direction 622).

In certain implementations, the bracket 620 is substantially tubular and/or extends at least partially around a longitudinal axis 626 of the bracket 620 and the transducer assembly 610 has a corresponding shape configured to fit within the bracket 620. For example, as schematically illustrates by FIGS. 7A-7B, the bracket 620 is tubular with a substantially circular cross-sectional shape and completely encircles the longitudinal axis 626, and the transducer assembly 610 is substantially cylindrical with a substantially circular cross-sectional shape. Other cross-sectional shapes (e.g., oval; polygonal with 3, 4, or more sides; geometric; non-geometric; regular; irregular) of the bracket 620 and the transducer assembly 610 are also compatible with certain implementations described herein.

In certain implementations, the second portion 634 applies at least one restoring force 640 to the inner surface 624 of the bracket 620 (e.g., a force in the outwardly radial direction). The at least one restoring force 640 is configured to generate at least one corresponding friction force configured to inhibit sliding of the transducer assembly 610 within the bracket 620 (e.g., along the sliding direction 622). During an implantation process, the apparatus 600 can initially be separate from the bracket 620 (e.g., while the fixation element 320 is being affixed to a portion of the recipient's body). Once the fixation element 320 is at least partially affixed to the recipient's body (e.g., by the practitioner), the apparatus 600 can be held using a tool (e.g., tweezers; not shown) that compresses the at least one arm 630 such that the second portion 634 is moved towards outer surface 612. For example, as schematically illustrated by FIG. 7A, the transducer assembly 610 can comprise a pair of arms 630 on opposite sides of the transducer assembly 610, and the tool can squeeze the second portions 634 of the two arms towards one another. The apparatus 600 can then be moved (e.g., by the practitioner) such that the transducer assembly 610 is received by (e.g., inserted into) the bracket 620. The apparatus 600 can then be slidably moved along the bracket 620 (e.g., by the practitioner). Once the transducer assembly 610 is at an operational position along the bracket 620, the tool can be removed from the at least one arm 630 (e.g., by the practitioner), thereby allowing the second portion 634 to press against the inner surface 624 of the bracket 620 so as to lock (e.g., self-lock; automatically lock) the transducer assembly 610 at the operational position (see, e.g., FIG. 7B).

Figure 8A:
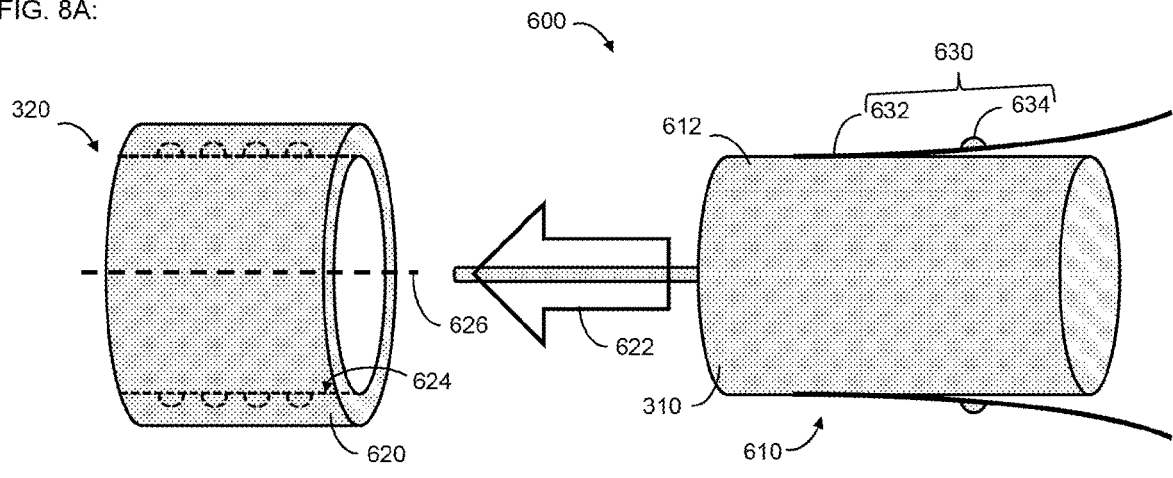
FIGS. 8A-8C schematically illustrate another example apparatus in accordance with certain implementations described herein.
Figure 8B:
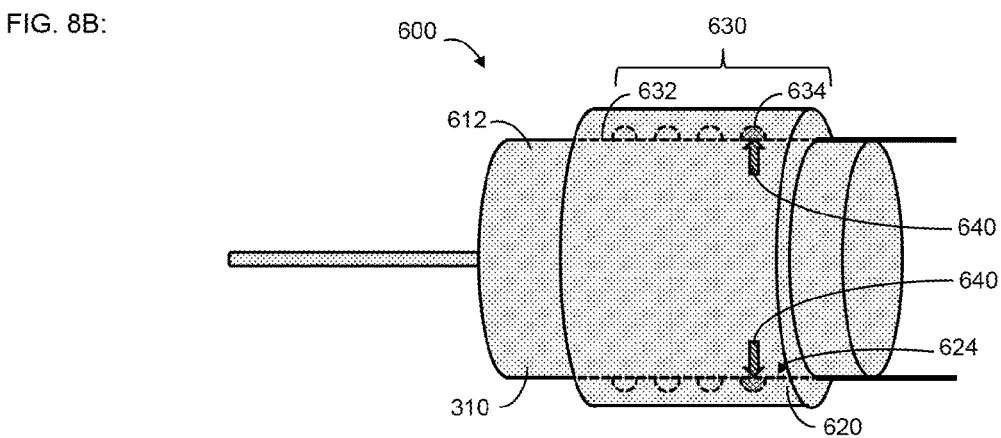
Figure 8C:
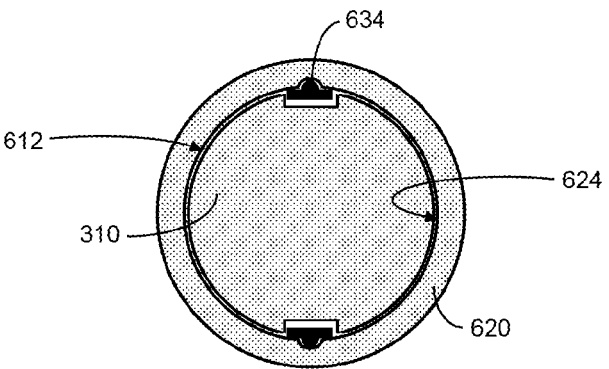

FIGS. 8A-8C schematically illustrate another example apparatus 600 in accordance with certain implementations described herein. FIGS. 8A and 8B shows the example apparatus 600 prior to and after being affixed, respectively, to the fixation element 320, and FIG. 8C shows a cross-sectional view of the example apparatus 600 of FIG. 8B. The example apparatus 600 of FIGS. 8A-8C is similar to that of FIGS. 7A-7B, with the second portion 634 of the at least one arm 630 comprising at least one first protrusion and/or recess configured to engage (e.g., mate) with and disengage from at least one second recess and/or protrusion positioned along the inner surface 624 of the bracket 620. For example, as schematically illustrated by FIGS. 8A-8C, the inner surface 624 of the bracket 620 comprises a plurality of recesses and each second portion 634 of two arms 630 comprises a corresponding protrusion configured to engage (e.g., mate) with one of the plurality of recesses. In certain implementations, the recesses of the inner surface 624 comprise slots (e.g., channels) that allow some rotation of the transducer assembly 610 within the bracket 620 about the longitudinal axis 626 of the bracket 620. The transducer assembly 610 in the first state has the at least one first protrusion and/or recess disengaged from the at least one second recess and/or protrusion and the transducer assembly 610 in the second state has the at least one first protrusion and/or recess engaged with the at least one second recess and/or protrusion.

During an implantation process, the apparatus 600 of FIGS. 8A-8C can initially be separate from the bracket 620 (e.g., while the fixation element 320 is being affixed to a portion of the recipient's body). Once the fixation element 320 is at least partially affixed to the recipient's body (e.g., by the practitioner), the apparatus 600 can be held using a tool (e.g., tweezers; not shown) that compresses the at least one arm 630 such that the second portion 634 is moved towards the outer surface 612. For example, as schematically illustrated by FIG. 8A, the tool can squeeze the two arms 630 towards one another such that the second portions 634 fit within the inner surface 624 (e.g., the most outwardly radial extent of the second portion 634 is less than the most inwardly radial extent of the inner surface 624). The apparatus 600 can then be slid into and slidably moved along the bracket 620 (e.g., by the practitioner). Once the transducer assembly 610 is at an operational position along the bracket 620, the tool can be removed from the at least one arm 630 (e.g., by the practitioner), thereby allowing the second portion 634 to press against the inner surface 624 of the bracket 620 so as to lock (e.g., self-lock; automatically lock) the transducer assembly 610 at the operational position (see, e.g., FIGS. 8B-8C). In certain implementations, the mating protrusions and recesses of the inner surface 624 and the at least one second portion 634 limit the positions of the transducer assembly 610 to a finite number and provide stronger locking of the apparatus 600 to the fixation element 320 than for an implementation utilizing only friction forces.

Figure 9:
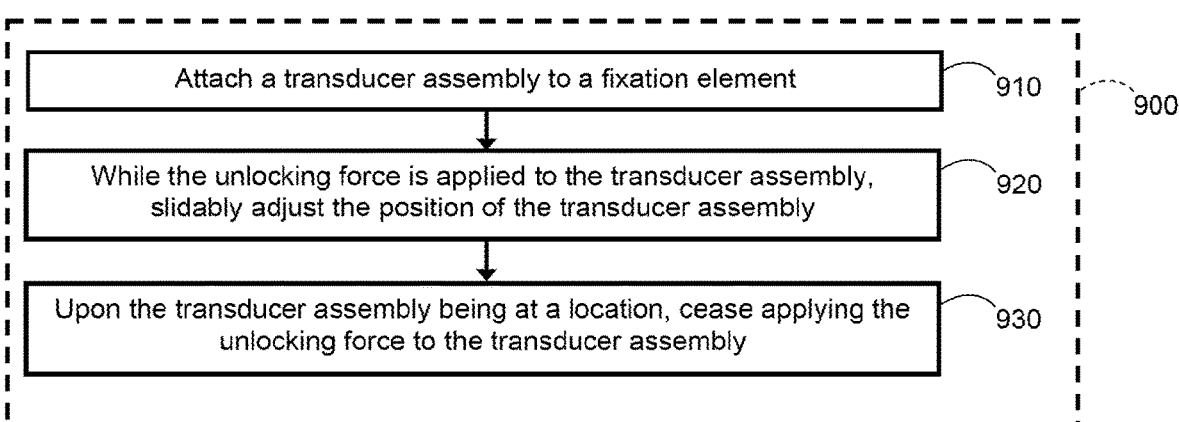
FIG. 9 is a flow diagram of an example method in accordance with certain implementations described herein.

FIG. 9 is a flow diagram of an example method 900 in accordance with certain implementations described herein. While the example method 900 is described herein by referring to the example apparatus 300, 600 of FIGS. 3A-3E, 4A-4B, 5A-5E, 6A-6B, 7A-7B, and 8A-8C, other apparatuses are also compatible with the example method 900 in accordance with certain implementations described herein. For example, the method 900 described herein can be applied to any of a variety of implantable medical devices.

In an operational block 910, the method 900 comprises attaching a transducer assembly (e.g., apparatus 300; transducer assembly 600) to a fixation element (e.g., fixation element 320; bracket 620) affixed to a location within a recipient's body. For example, said attaching is performed while an unlocking force (e.g., external force 350) is applied to the transducer assembly such that a position of the transducer assembly can be slidably adjusted relative to the fixation element. In certain implementations, the unlocking force is applied by a tool (e.g., tweezers; not shown) holding the transducer assembly (e.g., the tool being held by the practitioner). In certain other implementations, the practitioner receives the transducer assembly with the unlocking force being applied automatically (e.g., an elongate tool 420 or removable element 510 is within a region so as to inhibit the self-locking of the transducer assembly). In certain implementations, said attaching comprises moving the transducer assembly such that at least one retention element 520 of the transducer assembly is received by at least one recess of the fixation element.

In an operational block 920, the method 900 further comprises, while the unlocking force is applied to the transducer assembly, slidably adjusting the position of the transducer assembly relative to the fixation element such that the transducer assembly is at a location at which the transducer assembly is configured to be operationally coupled to a target portion of the recipient's body. In certain implementations, this slidably adjusting can be performed using a dummy transducer assembly to determine the operational location, and then the dummy transducer assembly can be removed and the actual (e.g., operational) transducer assembly can be attached to the fixation element and slidably adjusted to the operational location.

In an operational block 930, the method 900 further comprises, upon the transducer assembly being at the location, ceasing applying the unlocking force to the transducer assembly such that the transducer assembly self-locks to the fixation element at the location. For example, an elongate tool 420 or a removable element 510 can be withdrawn from the apparatus 300, 600 to cease applying the unlocking force to the transducer assembly, thereby allowing the at least one arm 330, 630 to contact and/or engage the fixation element 320.

In certain implementations, the method 900 further comprises, affixing the fixation element to the location within the recipient's body (e.g., prior to attaching the transducer assembly to the fixation element). For example, the practitioner can plastically deform the fixation element to adjust the position and/or orientation of the plurality of second mating elements 322 (e.g., to facilitate subsequent operational positioning of the transducer 310 facing the target portion of the recipient's body). In certain implementations, such adjustments can be performed with a dummy transducer assembly attached to the fixation element and once such adjustments are completed, the dummy transducer assembly can be replaced with the actual (e.g., operational) transducer assembly. By allowing such adjustments to be made to the fixation element without the transducer assembly attached to the fixation element, certain implementations reduce the probability of damaging the transducer assembly.

In certain implementations, the method 900 further comprises operationally coupling the transducer assembly to the target portion of the recipient's body. For example, once the transducer assembly is at the desired operational location, the practitioner can adjust an elongate member 312 (e.g., connection apparatus 216; rod; tube) of the transducer assembly and can affix a distal end of the elongate member

312 to the target portion of the recipient's body such that mechanical vibrations (e.g., generated by the transducer assembly or by the target portion) propagate along the elongate member 312 between the transducer assembly and the target portion.

Although commonly used terms are used to describe the systems and methods of certain implementations for ease of understanding, these terms are used herein to have their broadest reasonable interpretations. Although various aspects of the disclosure are described with regard to illustrative examples and implementations, the disclosed examples and implementations should not be construed as limiting. Conditional language, such as, among others, "can," "could," "might," or "may," unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

It is to be appreciated that the implementations disclosed herein are not mutually exclusive and may be combined with one another in various arrangements. In addition, although the disclosed methods and apparatuses have largely been described in the context of conventional auditory prostheses, various implementations described herein can be incorporated in a variety of other suitable devices, methods, and contexts. More generally, as can be appreciated, certain implementations described herein can be used in a variety of implantable medical device contexts that can benefit from having an adjustable orientation of at least a portion of the implanted device during implantation.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree. The ranges disclosed herein also encompass any and all overlap, sub-ranges, and combinations thereof. Language such as "up to," "at least," "greater than," "less than," "between," and the like includes the number recited. As used herein, the meaning of "a," "an," and "said" includes plural reference unless the context clearly dictates otherwise. Also, as used in the description herein, the meaning of "in" includes "into" and "on," unless the context clearly dictates otherwise.

While the methods and systems are discussed herein in terms of elements labeled by ordinal adjectives (e.g., first, second, etc.), the ordinal adjective are used merely as labels to distinguish one element from another (e.g., one signal from another or one circuit from one another), and the ordinal adjective is not used to denote an order of these elements or of their use.

The invention described and claimed herein is not to be limited in scope by the specific example implementations herein disclosed, since these implementations are intended as illustrations, and not limitations, of several aspects of the invention. Any equivalent implementations are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example implementations disclosed herein, but should be defined only in accordance with the claims and their equivalents.

What is claimed is:

1. An apparatus comprising:
at least one arm comprising:
  a first arm portion configured to be in mechanical communication with a transducer configured to be implanted within a recipient's body; and
  a second arm portion spaced from the first arm portion, the second arm portion comprising at least one first mating portion configured to engage and disengage with a plurality of second mating portions positioned along at least one longitudinal surface of a fixation element implanted within a portion of the recipient's body, the second arm portion configured to be moved between an unlocked state in which the at least one first mating portion is disengaged from the plurality of second mating portions and a locked state in which the at least one first mating portion is engaged with at least one of the second mating portions; and
at least one elastically deformable element configured to apply at least one restoring force to the at least one arm such that the second arm portion is in the locked state and to respond to at least one external force applied to the at least one arm such that the second arm portion is in the unlocked state.

2. The apparatus of claim 1, wherein the transducer is configured to be moved along the fixation element while the second arm portion is in the unlocked state and to be unmovable from a position along the fixation element while the second arm portion is in the locked state.

3. The apparatus of claim 1, wherein the at least one elastically deformable element comprises at least one spring mechanically coupled to the at least one arm.

4. The apparatus of claim 1, wherein the at least one elastically deformable element comprises a resilient portion of the at least one arm.

5. The apparatus of claim 1, wherein the at least one arm comprises a first arm comprising a first tab and a second arm comprising a second tab, the first and second arms configured to be positioned on opposite longitudinal surfaces of the fixation element, the first and second tabs configured to receive the at least one external force.

6. The apparatus of claim 5, wherein the first arm comprises a first pivot between the first tab and the second arm portion of the first arm, the second arm comprises a second pivot between the second tab and the second arm portion of the second arm, such that the first and second tabs respond to the at least one external force selectively applied to the first and second tabs by moving towards one another and by moving the second arm portions of the first arm and the second arm to the unlocked state.

7. The apparatus of claim 1, wherein the at least one arm at least partially bounds a hollow region configured such that insertion of an elongate tool into the hollow region by a practitioner applies the external force to the at least one arm.

8. The apparatus of claim 1, wherein the transducer is a microphone, an actuator, or an optical sensor.

9. The apparatus of claim 1, wherein the transducer is configured to be in operational communication with a target portion of the recipient's body, the target portion spaced from the fixation element.

10. The apparatus of claim 9, wherein the target portion comprises an ossicle, a portion of a cochlea, a portion of the otic capsule, or a semicircular canal of the recipient's body.

11. The apparatus of claim 1, wherein the fixation element is configured to be affixed to a portion of the recipient's skull.

12. An apparatus comprising:
a transducer assembly configured to be implanted within the recipient's body and received by a bracket of a fixation element configured to be implanted within a portion of a recipient's body, the transducer assembly comprising;
  a transducer configured to be implanted within a recipient's body; and
  at least one arm having a first portion mechanically coupled to an outer surface of the transducer assembly and a second portion spaced away from the first portion, the transducer assembly has a plurality of states comprising:
    a first state in which the at least one arm is elastically bent to be substantially straight along the outer surface such that the transducer assembly is configured to be inserted and/or adjustably slid within the bracket along a sliding direction; and
    a second state in which the second portion contacts an inner surface of the bracket and inhibits sliding of the transducer assembly within the bracket along the sliding direction.

13. The apparatus of claim 12, wherein the at least one arm comprises an elastically bendable leaf spring.

14. The apparatus of claim 12, wherein the second portion applies at least one restoring force to the inner surface of the bracket, the at least one restoring force configured to generate at least one corresponding friction force configured to inhibit sliding of the transducer assembly within the bracket along the sliding direction.

15. The apparatus of claim 12, wherein the at least one arm further comprises at least one first protrusion and/or recess configured to engage with and disengage from at least one second recess and/or protrusion positioned along the inner surface of the bracket, wherein the transducer assembly is in the first state when the at least one first protrusion and/or recess is disengaged from the at least one second recess and/or protrusion and is in the second state when the at least one first protrusion and/or recess is engaged with the at least one second recess and/or protrusion.

16. A method comprising:
attaching a transducer assembly to a fixation element affixed to a location within a recipient's body;
while an unlocking force is applied to the transducer assembly, slidably adjusting the position of the transducer assembly relative to the fixation element such that the transducer assembly is at a location at which the transducer assembly is configured to be operationally coupled to a target portion of the recipient's body; and upon the transducer assembly being at the location, ceasing applying the unlocking force to the transducer assembly such that the transducer assembly self-locks to the fixation element at the location.

17. The method of claim 16, wherein said attaching is performed while the unlocking force is applied to the transducer assembly.

18. The method of claim 16, further comprising, prior to said attaching, affixing the fixation element to the location within the recipient's body.

19. The method of claim 18, further comprising, prior to said attaching, plastically deforming the fixation element.

20. An apparatus comprising:

a fixation element configured to be affixed to a fixation location on and/or within a recipient's body, the fixation element comprising:

at least one surface; and a plurality of protrusions and/or recesses positioned along the at least one surface, the plurality of protrusions and/or recesses configured to engage and disengage with at least one recess and/or protrusion of at least one arm of a transducer assembly configured to be implanted within the recipient's body, the transducer assembly comprising a transducer configured to be in operational communication with a target portion of the recipient's body, the target portion spaced from the fixation location, the plurality of protrusions and/or recesses providing a plurality of discrete locations at which the transducer assembly can be selectively automatically locked to the fixation element.

21. The apparatus of claim 20, wherein the at least one arm of the transducer assembly comprises a first arm portion configured to be resiliently bent and/or rotated and a second arm portion spaced from the first arm portion and comprising the at least one recess and/or protrusion, wherein resiliently bending and/or rotating the first arm portion moves the second arm portion between an unlocked state in which the at least one recess and/or protrusion is disengaged from the plurality of protrusions and/or recesses and a locked state in which the at least one recess and/or protrusion is engaged with at least one of the plurality of protrusions and/or recesses.

22. The apparatus of claim 21, wherein the second arm portion in the locked state is configured to apply a force to the fixation element and the at least one arm is configured to respond to at least one external force applied to the at least one arm such that the second arm portion is in the unlocked state.

23. The apparatus of claim 20, wherein the at least one surface comprises two surfaces on opposite sides of the fixation element with corresponding subsets of the plurality of protrusions and/or recesses on opposite sides of the fixation element.

24. The apparatus of claim 20, wherein the fixation element comprises a first portion configured to be affixed to the fixation location, and a second portion extending from the first portion towards the target portion of the recipient's body.

25. The apparatus of claim 24, wherein the second portion is configured to be plastically deformed to modify a position and/or orientation of the at least one surface.

26. The apparatus of claim 20, wherein the fixation element further comprises at least one recess configured to receive at least one retention element of the transducer assembly such that the transducer assembly can be slidably adjusted among various positions along the fixation element away from the at least one recess.

27. The apparatus of claim 20, wherein the fixation element comprises a substantially tubular collar and the transducer assembly has a corresponding shape configured to be slid into and slidably moved within the collar.

28. The apparatus of claim 27, wherein the plurality of protrusions and/or recesses are positioned along an inner surface of the collar.

* * * * *